United States Patent [19]

Weissman

[11] Patent Number: 5,487,664
[45] Date of Patent: Jan. 30, 1996

[54] DENTAL POST PROVIDED WITH SUPPORT FRAME

[76] Inventor: Bernard Weissman, 225 E. 48th St., New York, N.Y. 10017

[21] Appl. No.: 292,259
[22] Filed: Aug. 18, 1994
[51] Int. Cl.$^6$ ...................................... A61C 5/08
[52] U.S. Cl. .......................... 433/221; 433/220; 433/224
[58] Field of Search ................................ 433/221, 220, 433/225, 172, 193, 224

[56] References Cited

U.S. PATENT DOCUMENTS

| | | | |
|---|---|---|---|
| 4,746,294 | 5/1988 | Colombo et al. | 433/174 |
| 4,752,225 | 6/1988 | Bori | 433/221 |
| 5,035,620 | 7/1991 | Roane | 433/221 |
| 5,073,112 | 12/1991 | Weil | 433/221 |

Primary Examiner—Cary E. O'Connor
Attorney, Agent, or Firm—Goodman & Teitelbaum

[57] ABSTRACT

A dental post having a support frame captured and interlocked thereon, and encaptured in a luting material, preferably such as a moldable self-curing tooth-colored composite material to create a laminated composite/metal foundation complex for retaining a dental rstoration securely on a tooth stub. The post includes a smooth cone-shape lower end portion for matchingly fitting into a prepared tooth canal, a threaded portion passively fitting in the tooth canal for engagement with the composite material, an unthreaded portion to provide greater strength, a square portion to permit the dental post to be unscrewed from the hardened composite material, a tapered portion, and a chisel-like portion at the upper end of the dental post. The support frame includes a pair of opposing legs for straddling the dental post and a bight portion connecting the legs together, the bight portion having a slot for receiving the chisel-like portion therethrough, a pair of pads extending transversely outwardly from the lower ends of the legs for seating in steps formed in the tooth stub, elongated slots formed in the legs to receive the composite material therethrough and to permit the bifurcated leg portions to be twisted to reinforce the structure of the legs. The chisel-like portion is inserted through the slot in the bight portion, and then turned 90 degrees to capture and interlock the dental post and the support frame together.

19 Claims, 1 Drawing Sheet

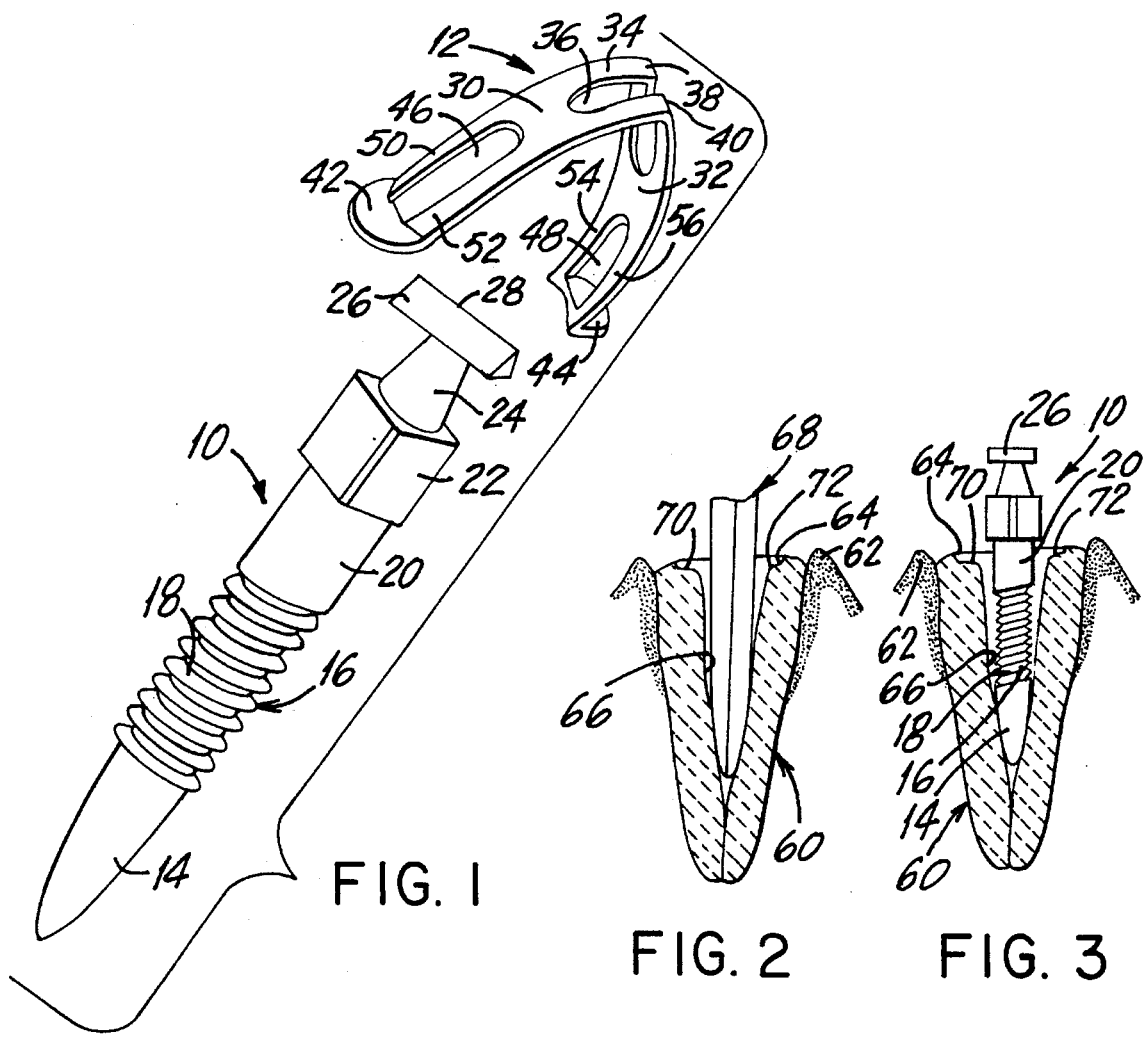

DENTAL POST PROVIDED WITH SUPPORT FRAME

BACKGROUND OF THE INVENTION

This invention relates to an anchor for supporting a dental prosthesis structure, and more particularly to a dental post for insertion into a tooth canal of a tooth stub, and a support frame captured and interlocked on an upper part of the dental post which extends upwardly from the tooth stub, being surrounded by a luting material, preferably such as a composite material to form a foundation complex for retention of a dental restoration provided thereon.

Dental posts are well known in the dental art. Teeth that have lost the coronal portion extending above the gum line through either accident, neglect or decay, in almost all instances require the removal of the nerve from the tooth canal by an endodontic obturation procedure, where the tooth canal is carefully explored and cleaned, with the apex thereof being securely sealed with an impermeable gutta percha material. Subsequent to such procedures, the tooth canal is often widened to a desired size and shape for the placement of either a prefabricated or custom cast metal dental post that will form the anchoring and supporting foundation for an artificial crown or jacket replacement.

Numerous dental posts have been suggested in the prior art. On some posts, there is provided an external thread to provide additional surface area in which the cement is received so as to improve the retention of the dental post within the tooth stub. However, though the threads formed on the prior art dental posts aid in the retention, at the same time, the threads reduce the diameter of the dental post which increases the risk of fracturing both during insertion and actual utilization of the dental post.

Though numerous dental posts for restoring teeth have been suggested in the prior art, there is no single post that presently provides the many essential elements for achieving the optimum performance thereof, such as providing a passive fit, retention resistance to horizontal shearing forces and the means for future retrieval thereof when it is necessary for re-entering the dental canal for retreatment procedures therein. Likewise, the prior art dental posts are presently missing the means of being able to accomplish such procedures aesthetically and economically, without utilizing the necessary costly laboratory technical procedures and multiple office visits. Therefore, there is a need for a dental post whose installation can be easily accomplished in a one-visit chairside procedure in a most economical manner, which is passively secured in the tooth canal to be compatible in form with natural root canal morphology, which has a strong supporting transverse structure and provides the major advantages of function, retention and reversibility, and which satisfies the major requirements of aesthetics, serviceability and economy.

SUMMARY OF THE INVENTION

Accordingly, it is an object of the present invention to provide an improved dental post which overcomes the problems of the prior art dental posts.

A further object of the present invention is to provide a dental post with increased retention capability in a tooth stub, as well as in the dental restoration provided thereon.

Another object of the present invention is to provide a dental post provided with a support frame which is resistant to horizontal shearing forces.

Still another object of the present invention is to provide a dental post provided with a support frame which permits future retrieval for re-entering the tooth canal for retreatment procedures therein.

Still a further object of the present invention is to provide a dental post provided with a support frame which is captured and interlocked thereon.

Yet another object of the present invention is to provide a dental post provided with a support frame which are surrounded and encaptured in a luting material, preferably such as a moldable, self-curing, tooth-colored composite material to create a laminated composite/metal foundation complex which is anchored in the tooth stub to receive an artificial crown or jacket thereon.

Still another object of the present invention is to provide a dental post provided with a support frame which provides simplified utilization, facilitates simple assembly, allows aesthetical and economical procedures which can be easily accomplished in a one-visit chairside procedure without utilizing costly laboratory technical procedures and multiple office visits which are usually necessary in the prior art.

Briefly, in accordance with the present invention, there is provided a dental post having a support frame captured and interlocked thereon, and surrounded and encaptured in a luting material, preferably such as a moldable self-curing tooth-colored composite material to create a laminated composite/metal foundation complex for retaining a dental restoration securely on a tooth stub. The post includes a smooth cone-shape lower end portion for matchingly fitting into a prepared tooth canal, a threaded portion passively fitting in the tooth canal for engagement with the composite material, an unthreaded portion to provide greater strength to resist the flexing and shearing forces acting upon the restored tooth, a square portion to permit the dental post to be unscrewed from the hardened composite material for retrieving the dental post from the tooth canal, a tapered portion, and a chisel-like portion at the upper end of the dental post for engagement with the support frame.

The support frame includes a pair of opposing legs for straddling the upper part of the dental post and a bight portion connecting the legs together, the bight portion having a slot for receiving the chisel-like portion therethrough for capturing and interlocking the dental post and support frame together, a pair of pads extending transversely outwardly from the lower ends of the legs for seating in steps formed in the tooth stub, elongated slots formed in the legs to receive the composite material therethrough and to permit the bifurcated leg portions to be twisted into a fixed turned position with respect to the pads to reinforce the structure of the legs to prevent bending thereof. The chisel-like portion of the dental post is inserted through the slot in the bight portion of the support frame, and then is turned 90 degrees to interlock the dental post and the support frame together.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which:

FIG. 1 is an exploded perspective view of the dental post and the support frame according to the present invention;

FIG. 2 is a cross sectional view through the tooth stub, showing a special square profiling reamer widening the tooth canal to a desired size and shape;

FIG. 3 is a cross sectional view similar to FIG. 2, showing the dental post positioned in the prepared tooth canal;

FIG. 4 is a cross sectional view similar to FIG. 3, showing the support frame positioned on the dental post;

FIG. 5 is a cross sectional view similar to FIG. 4, showing the support frame locked onto the dental post;

FIG. 6 is a cross sectional view similar to FIG. 5, showing a composite material disposed in the tooth canal to enclose the threaded portion of the dental post therein, and also surrounding the support frame, where the composite material has been prepared to provide a desirable form; and FIG. 7 is a cross sectional view similar to FIG. 6, showing a dental restoration disposed on and enclosing the composite material therein to provide a restored tooth.

In the various figures of the drawings, like reference characters designate like parts.

DETAILED DESCRIPTION OF THE PREFERRED EMBODIMENT

With reference now to the drawings, FIG. 1 shows a dental post 10 and a support frame 12 in accordance with the present invention. The dental post 10 is fabricated from a suitable metal material, and includes an elongated body having a smooth cone-shaped lower end portion 14 at one logitudinal end thereof, which matchingly fits into a prepared tooth canal as set forth below. The adjacent upwardly directed portion 16 has an external helical thread 18 formed about its outer surface to passively fit in the prepared tooth channel without making any engagement with the walls of the tooth channel as more fully described below. The next adjacent upwardly directed portion 20 is unthreaded and has the same diameter as the major diameter of the helical thread 18, so that the unthreaded portion 20 provides greater strength to resist the flexing and shearing forces acting upon the restored tooth.

The next adjacent upwardly directed portion 22 has a non-circular circumference so that portion 22 can be engaged with a tool for unscrewing the dental post 10, as will be mentioned below in fuller detail. Preferably, the portion 22 has a square configuration which can be engaged by a conventional square socket key well known in the art. The next adjacent upwardly directed portion 24 is tapered inwardly as it extends upwardly away from portion 22 to reduce the upper thickness thereof, the function of which will be discussed below.

Finally, the next upwardly directed portion 26 is disposed at the longitudinal top end of the dental post 10. The longitudinal length of the portion 26 extends transversely to the longitudinal axis of the dental post 10, to form a T-shaped arrangement with the tapered portion 24, and has a triangular cross section to provide a chisel-like construction with a transversely extending pointed upper edge 28, the function of which will be explained below. Furthermore, the longitudinal length of the chisel-like portion 26 is approximately the same length as the diagonal length of the square portion 22, but does not exceed same, so that the conventional square socket key can be inserted over the chisel-like portion 26 when engaging the square portion 22, as will be further discussed below.

The support frame 12 is preferably fabricated from a thin, highly resilient suitable metal material which is preferably coated with a tooth colored opaque material or is provided with a ceramic surface. Alternatively, the support frame 12 can be fabricated from a suitable plastic or ceramic material.

The support frame 12, which is formed in multiple linear directions to resist forces and to support and interlock with a composite material as set forth below, includes opposing legs 30, 32 connected together by a bight portion 34 to provide a V-shaped construction. However, it is understood, that the bight portion 34 could be arcuately curved to provide a U-shaped configuration, and even extended in length to increase the spacing between the legs 30, 32 for use in the larger back teeth, such as the molars. An elongated, longitudinally extending slot 36 is provided through the bight portion 34 so that the slot 36 extends downwardly from the apex of the bight portion 34 on opposite sides of the support frame 12. Accordingly, the slot 36 forms a pair of shoulders 38, 40 at the apex of the bight portion 34, the function of which will be explained below. It is noted, that the width of the slot 36 is approximately the same size, or slightly larger, as the width of the base of the chisel-like portion 26, and also the reduced uppermost thickness of the tapered portion 24.

A pair of feet or pads 42, 44 extend transversely outwardly in opposite directions away from each other from the lower ends of the legs 30, 32, respectively. Due to the adjustability of the support frame 12, where the legs 30, 32 can be bent towards or away from each other, the pads 42, 44 can be adjusted to the widest section of the tooth stub to create a wide support base to avoid shearing and dislodgement of the foundation complex, which will be described below, during the masticatory function and other functional and para-function jaw and tooth movements.

A pair of elongated, longitudinally extending slots 46, 48 are provided in the legs 30, 32, respectively, where the slots 46, 48 extend to the pads 42, 44, respectively, to bifurcate the legs 30, 32. As shown below, the composite material will extend through the slots 46, 48 to support and interlock the legs 30, 32 with the composite material. Furthermore, the slots 46, 48 permit the bifurcated portions 50, 52 of the leg 30 and the bifurcated portions 54, 56 of the leg 32 to be twisted into a fixed turned position with respect to the pads 42, 44, respectively, to reinforce the structure of the legs 30, 32 to prevent the legs 30, 32 from being transversely bent along the longitudinal length thereof.

With reference now to FIGS. 2–7, the assembly of the present invention with respect to a prosthetic structure will now be described, where the function and other aspects of the dental post 10 and the support frame 12 will become apparent. FIG. 2 shows a tooth stub 60 within the gum area 62, where the coronal portion of the tooth extending above the gum area has been lost through either accident, neglect or decay. The tooth has been initially cut down, typically to provide a suitable upper surface 64, and the nerve has been removed from the tooth canal 66 by an endodontic obturation procedure.

The tooth canal is carefully explored and cleaned to remove the pulp from the tooth canal 66, and then the apex of the tooth canal is securely sealed with an impermeable gutta perching material. A special square profiling reamer 68 is used to widen the tooth canal 66 to a desired predetermined size and shape to matingly match the smooth cone-shape lower end portion 14 of the dental post 10 so that the smooth cone-shape lower end portion 14 can be matchingly received therein. Additionally, a pair of opposing right angle steps 70, 72 are formed adjacent the tooth canal 66 in the ledge of the tooth stub 60 at the widest section of the tooth stub 60 extending from the lingual surface to the buccal surface.

Thereafter, as shown in FIG. 3, the dental post 10 is inserted into the tooth canal 66 in a snug matching arrangement so that the dental post 10 is supported in an upright position. In this position, the opposite ends of the chisel-like portion 26 face outwardly in the direction of the steps 70, 72 in the tooth stub 60, being in alignment therewith. It is noted, that only the smooth cone-shape lower end portion 14 engages the walls of the tooth canal 66 to thus prevent a corkscrew effect, where the threaded portion 16 fits passively in the tooth canal 66 so that the thread 18 on the threaded portion 16 does not engage the walls of the tooth canal 66. Furthermore, the unthreaded portion 20 of the dental post 10 is preferably positioned across the upper surface 64 of the tooth stub 60 to provide greater strength for resisting the flexing and shearing forces acting upon the restored tooth, as mentioned above.

The support frame 12 is now held over the dental post 10 so that the pads 42, 44 are in alignment over the respective steps 70, 72 in the tooth stub 60, where as mentioned above, the legs 30, 32 can be bent to adjust the position of the pads 42, 44 into an aligned position with the steps 70, 72, respectively. In this position, the elongated slot 36 in the bight portion 34 of the support frame 12 will be directly over and in alignment with the chisel-like portion 26 of the dental post 10. The support frame 12 is now lowered down onto the dental post 10 so that the pointed upper edge 28 of the chisel-like portion 26 guides the chisel-like portion 26 through the elongated slot 36.

Once the elongated slot 36 clears the chisel-like portion 26, the pads 42, 44 will come to rest in the respective steps 70, 72 so that the legs 30, 32 of the support frame 12 straddle the upper part of the dental post 10, as shown in FIG. 4. It is understood, that the depth of the steps 70, 72 in the tooth stub 60 can be reformed in order to obtain the proper position of the support frame 12 as shown in FIG. 4. Furthermore, due to the increasing downward taper of the tapered portion 24, the slot 36 is engaged at the reduced uppermost thickness of the tapered portion 24 adjacent to the chisel-like portion 26, and is prevented from sliding further down the tapered portion 24.

The dental post 10 is now turned 90 degrees, in either direction, to capture and interlock the support frame 12 on the dental post 10, as shown in FIG. 5, to prevent any side and upward dislodgement thereof from the dental post 10. In this position, the bight portion 34 is held captured on the reduced uppermost thickness of the tapered portion 24, with the undersurface of the wide base of the chisel-like portion 26 being engaged on the shoulders 38, 40 at the apex of the bight portion 34 of the support frame 12 to provide for the retainment thereof in order to maintain the support frame 12 and the dental post 10 firmly in place during the subsequent laminating and luting procedures, as set forth below. It is noted, that the pads 42, 44 are firmly seated in the respective steps 70, 72 to provide a wide support base against shearing and dislodgement of the foundation complex, set forth below, during the masticatory function and othr functional and para-function jaw and tooth movements.

The support frame 12 and the dental post 10 are now surrounded and encaptured in a moldable, self-curing, tooth-colored composite material 74, or any other suitable luring material, such being well known in the dental art, where the composite material 74 extends into the tooth canal 66 around the threaded portion 16. The composite material 74 is built-up in a conventional manner well known in the art and alllowed to harden to create, in combination with the dental post 10 and the support frame 12, a laminated composite/metal foundation complex 76 which is anchored in the tooth stub 60. The built-up hardened composite material 74 is then prepared with conventional diamond instruments to a desirable form, as shown in FIG. 6, to provide a foundation for an artificial crown or jacket.

It is noted, in an alternate method, that the dental post 10 and the support frame 12 can first be interlocked together as mentioned above, and then inserted into the tooth canal 66 as an assembled unit, as shown in FIG. 5, thus by passing the steps shown in FIGS. 3 and 4. Likewise, the dental post 10 and the support frame 12 can first be interlocked together as an assembled unit, in the manner set forth above, and then surrounded by the composite material 74, and thereafter be inserted into the tooth canal 66 so that the composite material 74 can be built-up and allowed to harden, and then prepared to the desirable form as shown in FIG. 6.

Once the foundation complex 76 is formed, as shown in FIG. 6, the prosthetic structure or dental restoration 78, such as an artificial crown or jacket, is suitably provided on the upper surface 64 of the tooth stub 60 to enclose the foundation complex 76 therein, as shown in FIG. 7, in accordance with standard techniques well known in the dental art to provide a desirable form having an aesthetic tooth-colored background compatible with present day requirements for reflective porcelain crowns and jackets.

It is noted, that the above mentioned preparation and installation can be easily accomplished in a one-visit chair-side procedure in a most economical manner. Thus, the combination of the passively cemented dental post, which is compatible in form with natural root canal morphology, together with the strong supporting transverse frame, and the strong, widely used composite materials provide the major advantages of function, retention and reversibility. The described dental post 10 design, the transverse support frame 12 structure and the composite material 74, forming the foundation complex 76, together with the jacket crown 78 are the essential elements for restoring the effected teeth, and satisfies the major requirements of asthetics, serviceability and economy.

It is further noted, that the dental post 10 can be safely retrieved from the tooth canal 66 at any time. Accordingly, first the jacket crown 78, the upper portion of the composite material 74, and the support frame 12 are removed. Then, in a conventional manner well known in the dental art, the composite material 74 surrounding the square portion 22 of the dental anchor 10 is cleared away to expose the upper part of the dental anchor 10. The above mentioned square socket key is then inserted over the chisel-like portion 26 at the free upper end of the dental post 10 into engagement with the square portion 22 for unscrewing the post (counter clockwise) from the hardened composite material 74 surrounding the threaded portion 16 in the root canal 66 without damaging the tooth stub 60.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental post for retaining a dental restoration on a prepared tooth stub having a canal therein, said dental post comprising:

an elongated body;

first means for matchingly fitting into the tooth canal, said first means including a smooth cone-shaped lower end portion;

second means for coacting with a securing material to prevent said dental post from being pulled out of the tooth canal, and also for permitting said dental post to be retrieved from the tooth canal, said second means including a threaded portion for engagement with the securing material while allowing said threaded portion to be unscrewed from the securing material for removing said dental post from the tooth canal;

third means for facilitating the unscrewing of said threaded portion from the securing material, said third means being a non-circular portion;

said threaded portion being disposed between said smooth cone-shaped lower end portion and said non-circular portion; and engagement means being disposed at a free top end of said elongated body for interlocked engagement with a support frame disposed on the tooth stub and straddling an upper part of said dental post, said engagement means including a chisel-like portion.

2. A dental post according to claim 1, wherein said non-circular portion has a square configuration.

3. A dental post according to claim 1, including fourth means to provide strength to said post body to resist flexing and shearing forces acting upon the dental restoration, said fourth means including an unthreaded portion disposed between said threaded portion and said non-circular portion, said unthreaded portion having a diameter equal to a major diameter of said threaded portion.

4. A dental post according to claim 1, wherein a tapered portion is disposed between said chisel-like portion and said non-circular portion with said tapered portion being reduced in thickness toward said chisel-like portion, said chisel-like portion extending transversely to longitudinal axis of said elongated body to provide a transversely extending pointed upper edge equal in length to maximum width of said non-circular portion.

5. A support frame for a dental post to retain a dental restoration on a prepared tooth stub having a canal therein, said support frame comprising:

a pair of opposing first and second legs for straddling an upper part of the dental post;

a bight portion connecting said first and second legs together;

opening means extending through said bight portion for receiving an upper portion of the dental post therethrough; and shoulder means provided on said bight portion on opposite sides of said opening means for engaging the upper portion of the dental post to capture and interlock said support frame and the dental post together after the upper portion has been inserted through said opening means and the dental post has been turned ninety degrees relative to said bight portion.

6. A support frame according to claim 5, wherein said bight portion has an apex to provide said support frame with a V-shaped configuration.

7. A support frame according to claim 5, wherein pad means are provided on lower ends of said legs in a transverse arrangement with said legs for seating in steps provided in the tooth stub adjacent to the tooth canal.

8. A support frame according to claim 5, wherein an elongated longitudinally extending slot is provided in each of said legs to bifurcate said legs.

9. A support frame according to claim 8 wherein each bifurcated leg portion of each of said legs is twisted into a fixed turned position to provide a reinforced leg structure for each of said legs to prevent transverse bending thereof.

10. A dental post and support frame assembly for retaining a dental restoration on a prepared tooth stub having a canal therein, said assembly comprising:

said dental post having an elongated body with a lower first end portion for inserting into the tooth canal, and an opposite upper second end portion;

said support frame including a pair of opposing first and second legs for straddling an upper part of said dental post and a bight portion connecting said first and second legs together; and said support frame being provided with engagement means for coacting with said second end portion of said dental post to capture and interlock said support frame and said dental post together.

11. An assembly according to claim 10, wherein said engagement means includes opening means extending through said bight portion for receiving said second end portion therethrough, and shoulder means on opposite sides of said opening means for engaging an underside of said second end portion after said second end portion has been inserted through said opening means and said dental post has been turned ninety degrees relative to said bight portion.

12. An assembly according to claim 11, wherein said second end portion has a chisel-like construction extending transversely to longitudinal axis of said post body of provide a transversely extending pointed upper edge.

13. An assembly according to claim 12, wherein a tapered portion of said post body is disposed adjacent to said second end portion with said tapered portion being reduced in thickness towards said second end portion to provide a reduced thickness portion at said second end portion for capturing said bight portion thereon.

14. An assembly according to claim 10, wherein said lower first end portion has a smooth cone-shaped configuration for matchingly fitting into the tooth canal.

15. An assembly according to claim 10, wherein said post body includes first means for coacting with a securing material to prevent said dental post from being pulled out of the tooth canal, and also for permitting said dental post to be retrieved from the tooth canal, said first means including a threaded portion for engagement with the securing material while allowing said threaded portion to be unscrewed from the securing matertial for removing said dental post from the tooth canal, said post body also including second means for facilitating the unscrewing of said threaded portion from the securing material, said second means being a non-circular portion.

16. An assembly according to claim 15, wherein said non-circular portion has a square configuration, said second end portion having a transverse length equal to a diagonal of said non-circular portion.

17. An assembly according to claim 10, wherein said bight portion has an apex to provide said support frame with a V-shaped configuration.

18. An assembly according to claim 10, wherein pad means are provided on lower ends of said legs in a transverse arrangement with said legs for seating in steps provided in the tooth stub adjacent to the tooth canal.

19. An assembly according to claim 10, wherein an elongated longitudinally extending slot is provided in each of said legs to bifurcate said legs, each bifurcated leg portion of each of said legs being twisted into a fixed turned position to provide a reinforced leg structure for each of said legs to prevent transverse bending thereof.

* * * * *